(12) United States Patent
Starke

(10) Patent No.: US 7,970,474 B2
(45) Date of Patent: Jun. 28, 2011

(54) FILTER FEEDTHROUGH FOR IMPLANTS

(75) Inventor: Marcel Starke, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 855 days.

(21) Appl. No.: 11/877,773

(22) Filed: Oct. 24, 2007

(65) Prior Publication Data

US 2008/0119906 A1 May 22, 2008

(30) Foreign Application Priority Data

Nov. 17, 2006 (DE) .......................... 10 2006 054 249

(51) Int. Cl.
*A61N 1/08* (2006.01)
(52) U.S. Cl. ......................................................... 607/37
(58) Field of Classification Search .................... 607/36, 607/37
See application file for complete search history.

(56) References Cited

U.S. PATENT DOCUMENTS

| | | | |
|---|---|---|---|
| 5,333,095 A | 7/1994 | Stevenson et al. | |
| 5,620,476 A | 4/1997 | Truex et al. | |
| 5,683,435 A | 11/1997 | Truex et al. | |
| 5,759,197 A | 6/1998 | Sawchuk et al. | |
| 5,836,992 A | 11/1998 | Thompson et al. | |
| 6,516,808 B2 * | 2/2003 | Schulman ..................... | 128/899 |
| 6,999,818 B2 * | 2/2006 | Stevenson et al. ............. | 607/37 |
| 2003/0179536 A1 | 9/2003 | Stevenson et al. | |
| 2005/0219787 A1 | 10/2005 | Stevenson et al. | |
| 2006/0247714 A1 | 11/2006 | Taylor | |

FOREIGN PATENT DOCUMENTS

| | | |
|---|---|---|
| DE | 19957189 | 11/1999 |
| WO | WO 2004/105572 | 12/2004 |

OTHER PUBLICATIONS

European Search Report, dated Dec. 28, 2007.
German Search Report, dated Jul. 18, 2007.

\* cited by examiner

*Primary Examiner* — Carl H Layno
*Assistant Examiner* — Brian T Gedeon
(74) *Attorney, Agent, or Firm* — ARC IP Law, PC; Joseph J. Mayo

(57) ABSTRACT

A new hermetically-sealed contact feedthrough for cardiac pacemakers and defibrillators for the connection between internal device electronics and external components, a flat ceramic disk (1) being used as an insulating main carrier, in which openings (3) are situated, into which various electrode embodiments (4, 5, 6, 7) may be inserted as through contacts. Using a metal flange or metal-plated vapor deposition zone (2), the ceramic disk may be soldered directly onto the implant housing (11). In addition, active and passive auxiliary components (8) may be applied directly to the ceramic. The main carrier may be implemented as a multilayer ceramic (9), so that rewiring levels and shielding components (10) may be integrated in the feedthrough. The feedthrough according to the present invention allows novel construction variants, above all things having orientation to multipolar systems, through use of standardized ceramic semifinished products.

9 Claims, 5 Drawing Sheets

US 7,970,474 B2

FILTER FEEDTHROUGH FOR IMPLANTS

This application takes priority from German Patent Application DE 10 2006 054 249.5, filed 17 Nov. 2006, the specification of which is hereby incorporated herein by reference.

BACKGROUND OF THE INVENTION

1. Field of the Invention

The present invention is in the field of medical implants having electronic components, such as cardiac pacemakers, defibrillators, cardioverters, neurostimulators, or auditory canal implants. In particular, the present invention relates to the hermetically sealed feedthroughs required in devices of this type for the various electrical connections between internal device electronics and external components. In a special embodiment, the present invention relates to the shielding and/or filtering of electromagnetic interference (EMI) required for such feedthroughs.

Furthermore, the present invention relates to manufacturing method for producing the components according to the present invention.

2. Description of the Related Art

Implantable devices typically comprise a metal housing having a plug connection incorporated therein for receiving external connections, e.g., for electrical stimulation or measuring physiological signals. The hermetic seal of the components situated in the internal area (control electronics, battery) in relation to the environmental conditions, as exist in the inside of the body of the wearer, is of special significance. This places special demands on the feedthroughs of the electrical connections. No corrosion effects may occur here, each individual through contact must be absolutely tight to gas and liquid diffusion.

The prior art is that insulators made of ceramic are used as a carrier in feedthroughs for implants. These are predominantly shaped cylindrically and compressed and sintered as molded parts. As a rule, the electrical through contact is produced via prefinished openings in the ceramic using metallic contact pins (pins). The attachment capability to the implant housing is provided for the ceramic insulator in turn via a metallic flange. Thin, insulation ceramic, and flange are situated in such a way that the pins are enclosed by the ceramic and the ceramic is in turn enclosed by the flange. Such a feedthrough is described, for example, in the documents U.S. Pat. Nos. 5,759,197 and 5,836,992. FIG. 1 shows such a configuration according to the prior art.

Ceramic, flange, and pins are typically soldered hermetically sealed by a brazing process using gold solder. For this purpose, the insulation ceramic must be partially metal-plated beforehand on the soldered surfaces. This coating technology is complex, because individual masks must be used for it. The shape described and the specialization of the individual steps therefore prevent cost-effective manufacturing methods and the use of cost-effective semifinished products for feedthroughs according to the prior art.

Notwithstanding the construction described, alternative approaches are known from the documents U.S. Pat. Nos. 5,620,476 and 5,683,435. Instead of individual feedthroughs having one pin each, narrow ceramics in multilayer construction are used therein. A number of varying electrical feedthrough contacts are applied here as printed conductors to internal layers of the multilayer ceramic. The strip-shaped multilayer ceramic is in turn annularly enclosed by an oval flange, similarly to the contact pin in the conventional construction described, and thus soldered into the housing of the implant as a vertical collective feedthrough. Numerous individual processes and coatings are also required in this technique. In particular, sealing the vertically inserted multilayer ceramic places special demands on the precise fit of the annularly enclosing flange and the peripheral metal plating of the ceramic for the soldering process.

A further problem in feedthroughs for implantable devices is the susceptibility to electrical interference from interference by external electromagnetic fields. Because of the rising amplifier sensitivity on one hand and the increasing external interfering influences on the other hand (radio into the gigahertz range, mobile telephones having strong transmission power operated in the proximity), the demands grow on shielding by EMI filtering. For good filtering, passive or active components must be positioned proximally to the direct inputs and be electrically contacted with the pins and the flange and/or another potential.

The present invention proceeds from the described prior art. It is based on the object of providing an alternative feedthrough, which may be produced cost-effectively and which meets the cited requirements in regard to a hermetically tight incorporation on the implant housing and shielding capabilities. It is based on the further object of providing a manufacturing method for producing a feedthrough according to the present invention. These objects are fulfilled in a feedthrough as claimed herein. Further advantages and special designs of the feedthrough according to the present invention and the manufacturing method are claimed herein.

BRIEF DESCRIPTION OF THE FIGURES

The present invention is explained in greater detail in the following on the basis of preferred exemplary embodiments with reference to the drawings and the reference numerals used therein.

DETAILED DESCRIPTION OF THE INVENTION

To be able to produce feedthroughs cost-effectively in the standard manufacturing method, the overall construction must be adapted to standard manufacturing processes. The present invention therefore suggests the use of flat ceramics, which may be produced using known methods. Green ceramics such as unfired LTCC (low-temperature cofired ceramics) or unfired HTCC (high temperature cofired ceramics) are preferably suitable as starting materials. Furthermore, $Al_2O_3$ ceramics are preferably usable.

Figure 1:
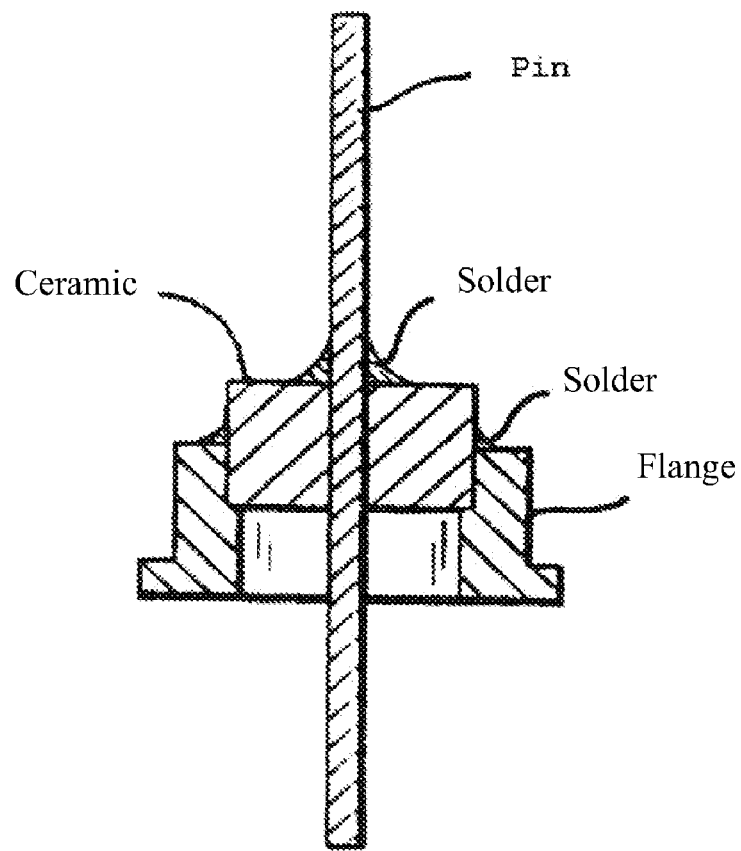
FIG. 1 shows a feedthrough for implants according to the related art.
Figure 2:
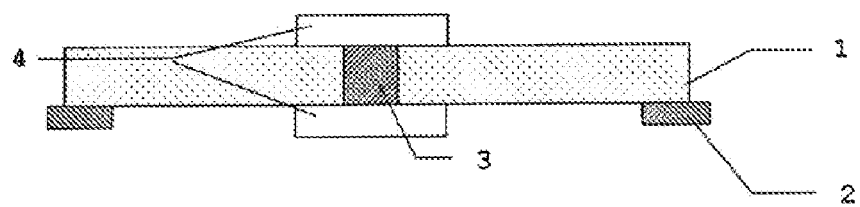
FIG. 2 shows an embodiment of the feedthrough according to the present invention (section).

FIG. 2 shows the construction of a first embodiment of the feedthrough according to the present invention as a schematic section. A flat ceramic (1) is used as an insulator here, which may be connected via a flange (2) to the implant housing, e.g., using a soldering process, for example. Due to the special construction of the ceramic, it is possible to dispense with the flange and solder the ceramic directly onto the implant housing using metal plating of the edge area.

For the through contact, the ceramic has an opening (3). Openings of this type are to be produced by a via technology, for example, i.e., the ceramic is drilled in standard technologies or punched before a firing process and the hole is filled up by metal pastes and thus an electric through contact is provided.

Contact surfaces (4) are situated on both sides of the opening on the ceramic in the example of FIG. 2. As an alternative embodiment, a solder ball (5) is applied on one side instead of the contact surface in FIG. 2a. FIG. 2b shows the feedthrough according to the present invention having a nail head contact (6), and FIG. 2c having a typical pin contact (7).

Figure 2A:
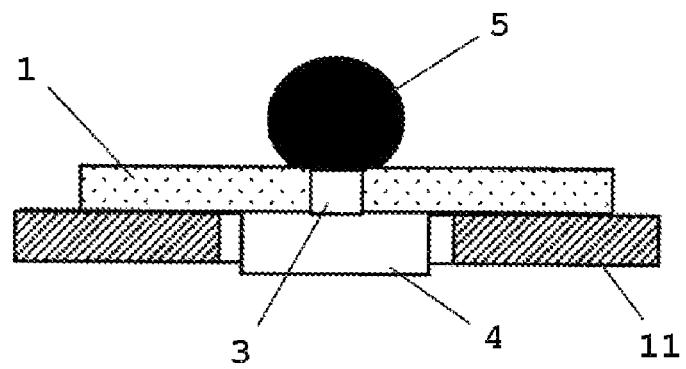
FIG. 2a shows the feedthrough from FIG. 2 having solder ball.
Figure 2B:
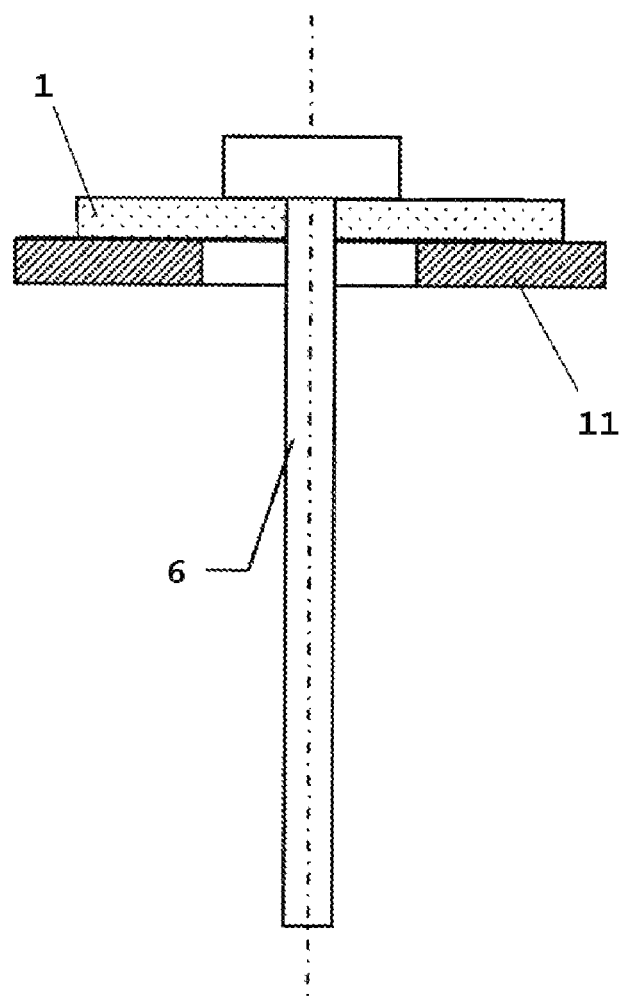
FIG. 2b shows the feedthrough from FIG. 2 having nail head.
Figure 2C:
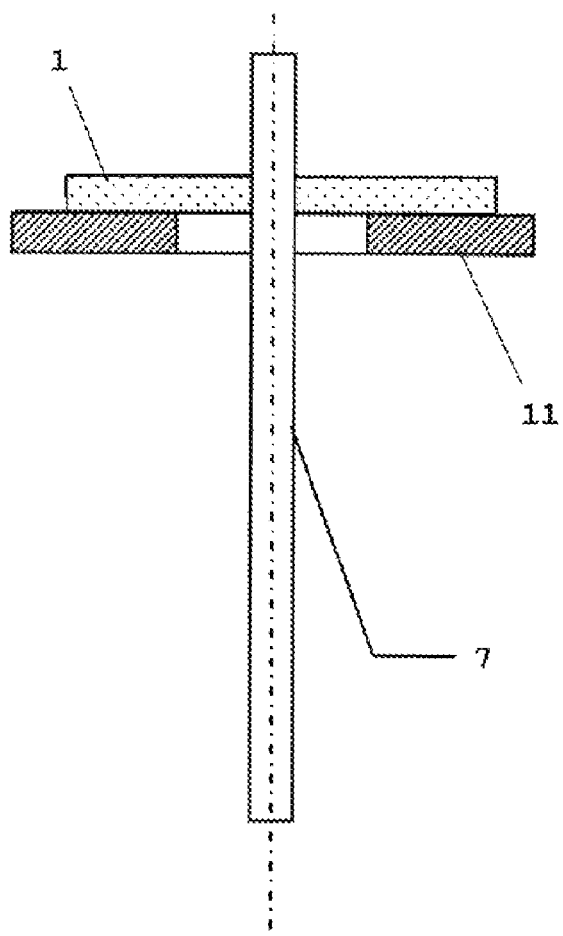
FIG. 2c shows the feedthrough from FIG. 2 having pin.

In the exemplary embodiments according to FIGS. 2a, 2b, and 2c, the flange is replaced by a metallic coating and the ceramic (1) is connected to the implant housing (11) via this coating.

The advantage of the coating according to the present invention is that—in contrast to the feedthroughs having complicated constructions typical up to this point—it may be produced using a simple method, which is based on well-known method sequences. The manufacturing method for producing the contact feedthrough according to the present invention has the following sequence of steps:

providing a flat ceramic,
structuring the flat ceramic to provide multiple flat ceramic disks (1) which are suitable to be used as carriers,
coating the flat ceramic to provide soldering surfaces,
providing a soldered connection on the soldering surfaces,
isolating the ceramic disks.

The advantage of this manufacturing method is that multiple flat ceramic disks (1)—which form the main body of the finished contact feedthrough according to the present invention—may be produced from a prefinished flat ceramic in a sheet, in particular in a multiple sheet structure. Depending on the size of the prefinished flat ceramic and the desired number of ceramic disks (1), more than 20, preferably 20 to 100, especially preferably 20 to 50 feedthroughs according to the present invention may be produced in a sheet. Therefore, a large number of contact feedthroughs may be produced significantly more easily, rapidly, and using a high degree of automation. A further advantage is that a test for hermetic seal (using HE leak testers, for example) and/or electromagnetic compatibility may still be performed in the sheet before the last method step (isolation of the ceramic disks).

The second work step of the manufacturing method sequence "structuring the flat ceramic" preferably contains the work step "producing at least one opening". The opening (3) may be produced by material-removing drilling or by chipless lasering or punching. Other suitable material-removing or chipless methods also come into consideration for this work step. The opening (3) is used to allow an electrical contact (4, 5, 6, 7) from the interior of a housing to the outside of the housing.

According to the present invention, the flat ceramic is structured using punching, lasers, notching, or another method known to those skilled in the art.

The coating is used to provide soldering surfaces to be able to electrically connect active and/or passive components (8) such as capacitors, oils, or microchips. These active and/or passive components are used for shielding the housing interior from external electromagnetic radiation and/or for transmitting HF signals for telemetry over large distances. Chips having integrated transceiver parts are used to transmit the HF signals. It has been shown to be advantageous to place these telemetry components directly on a contact feedthrough, because the transmission of HF signals into the implant housing and out of this housing is made significantly easier by avoiding the implant housing. HF signals may thus be transmitted using a significantly lower transmission power, which increases the service life of the implant.

This equipping of the components occurs after the production of a solder connection and comprises the manufacturing step "soft soldering of the components" to produce an electrical contact. The soldering surfaces may also be used for the electrical connection between a weldable flange and a contact (4, 5, 6, 7). Therefore, the soldering surfaces are suitable for brazing or soft soldering, for example, on the basis of niobium or titanium, because the flange and the feedthrough have to be soldered hermetically sealed, which is not ensured in a soft soldering method. The use of electrically conductive adhesives is also conceivable.

The coating for the soldering surfaces are produced easily and suitably for automatic methods with the aid of templates.

Figure 3:
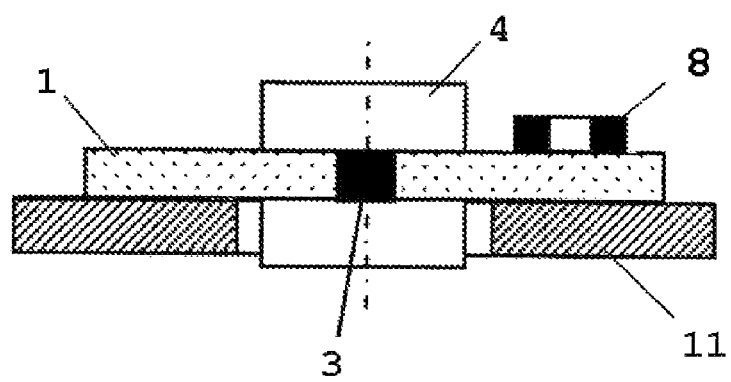
FIG. 3 shows a feedthrough having a capacitor for EMI filtering.
Figure 4:
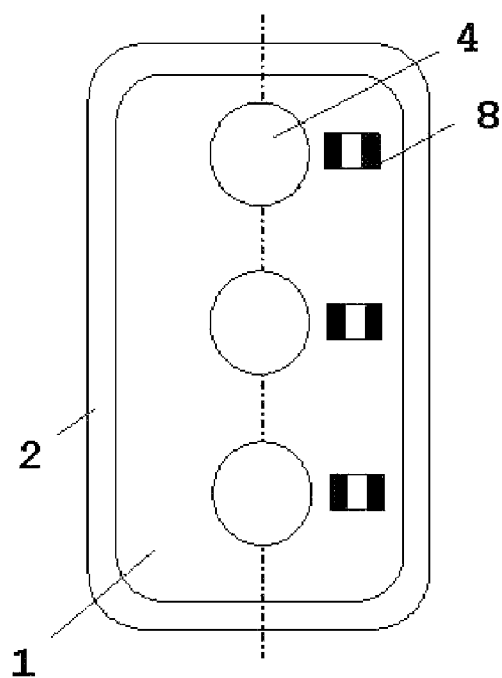
FIG. 4 shows the feedthrough from FIG. 3 (top view) having three contacts.

FIG. 3 shows an expanded embodiment of the ceramic feedthrough in which further components are carried by the ceramic. In this example, a capacitor (8), which is used for EMI filtering, for example, is applied on an equipping side as an SMT component (surface-mount technology). FIG. 4 shows a corresponding top view of such an embodiment having three contact surfaces (4) situated adjacent to one another and the assigned capacitors (8). The electrical connections of the capacitors, e.g., to the attachment flange, may be produced by printed conductors vapor-deposited on the ceramic surface, for example (not shown). Standard methods of electronics may be used for such equipping with active and passive elements (SMT equipping in the sheet using "pick & place" devices).

Figure 5:
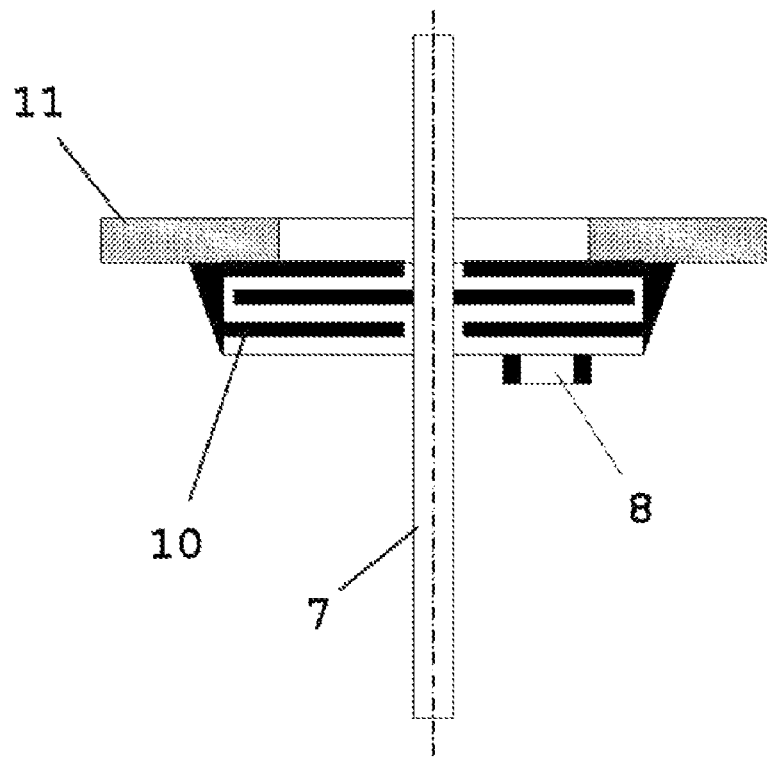
FIG. 5 shows an embodiment as a multilayer ceramic having metal plating layers.
Figure 6:
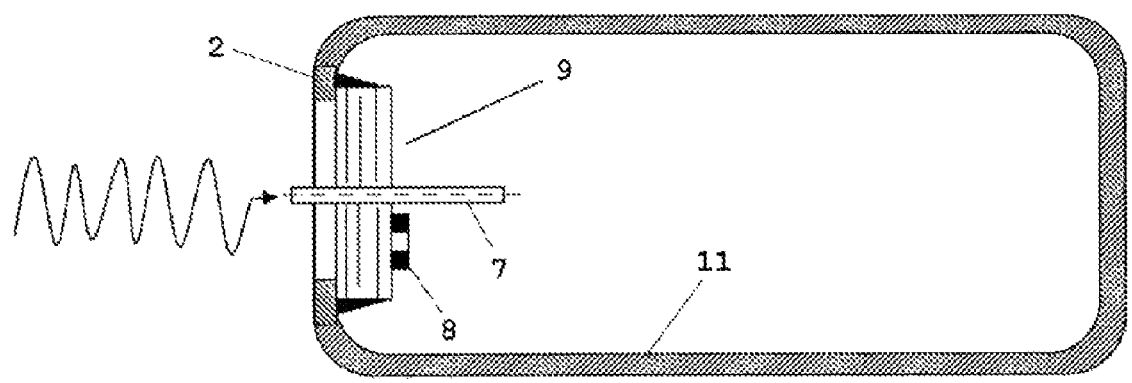
FIG. 6 shows the shielding effect after use on the implant housing.

Both compact, single-layer ceramic disks, and also multilayered ceramics may be used as the insulator. In multilayered ceramics, wiring levels may be introduced into the intermediate layers of the ceramic, which may also be used for contacting active and passive components (8). FIG. 5 shows such an embodiment of the present invention having a multilayer ceramic (9). A further advantage of this embodiment is the additional shielding effect. For this purpose, additional metal plating levels (10) may be introduced, which are electrically connected to the potential of the conductive implant housing (11), for example, so that a Faraday cage is formed. If the metal-plated ceramic layers are designed as correspondingly thin to one another, a flat capacitor results, which works as an input filter. The filter effect on special frequency ranges (wavelength $\lambda$ of the incident interfering signals) may thus be optimized in that a suitable spacing of the layers is predefined (for example: layer spacing D as integral fraction of the wavelength: $D=\lambda/2, \ldots, \lambda/100$).

The feedthrough according to the present invention allows novel construction variants through the use of ceramic semi-finished products, above all things having orientation to multipolar systems. The feedthrough offers a high design flexibility and independence from special tools. In addition, through the construction of the feedthrough according to the present invention, circuit elements may be used easily and cost-effectively directly on the insulator ceramic in standard technology. If multiple layers are used, shielding components and rewiring levels may be integrated in the feedthrough, the construction allowing a cost-effective automated application of flat technologies (paste printing, simple mask technologies).

What is claimed is
1. A method for producing a contact feedthrough comprising:
- providing a flat ceramic;
- structuring said flat ceramic to provide multiple flat ceramic disks which are capable of being used as a carrier (1) to be electrically connected to a housing (11) of an implantable device wherein said carrier (1) is configured so that said housing (11) of said implantable device does not enclose said carrier (1);
- coating said multiple flat ceramic disks with metal to provide soldering areas;
- providing a soldered connection on said soldering areas; and,
- isolating said multiple flat ceramic disks from each other.

2. The method according to claim 1, wherein said structuring of said flat ceramic further comprises:
- producing at least one opening (3), which is capable of passing a contact (4, 5, 6, 7) through.

3. The method according to claim 1 wherein said structuring of said flat ceramic is performed by punching, lasers, or notching.

4. The method according to claim 1, wherein said coating is performed with aid of masks or templates.

5. The method according to claim 1, wherein after said providing said soldered connection, coupling contacts (4, 5, 6, 7) with active and/or passive electrical components (8).

6. The method according to claim 5, further comprising providing shielding a housing interior from external electromagnetic radiation and/or for transmitting HF signals for telemetry over large distances using said active and/or passive electrical components (8).

7. The method according to claim 1, wherein said providing said flat ceramic comprises providing a multilayer ceramic capable of being used as said carrier (1).

8. The method according to claim 7, wherein said providing said multilayer ceramic (9) comprises providing said multilayer ceramic (9) comprising at least one internal layer, which is configured as a wiring level for connecting said active and/or passive electrical components (8).

9. The method according to claim 8, wherein said providing said multilayer ceramic (9) comprising at least one internal layer comprises providing a capacitor area in said at least one internal layer.

* * * * *